US011484295B2

(12) United States Patent
Sakai et al.

(10) Patent No.: US 11,484,295 B2
(45) Date of Patent: Nov. 1, 2022

(54) ULTRASOUND DIAGNOSTIC TECHNIQUE FOR SETTING VIRTUAL ORIGINS OF ACOUSTIC LINES FOR TRAPEZOIDAL SCANNING

(71) Applicant: Konica Minolta, Inc., Tokyo (JP)

(72) Inventors: Tomohito Sakai, Kanagawa (JP); Akihiro Kawabata, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 20 days.

(21) Appl. No.: 16/788,504

(22) Filed: Feb. 12, 2020

(65) Prior Publication Data

US 2020/0268357 A1    Aug. 27, 2020

(30) Foreign Application Priority Data

Feb. 21, 2019    (JP) .............................. JP2019-029803

(51) Int. Cl.
*A61B 8/00* (2006.01)
*A61B 8/14* (2006.01)
*A61B 8/08* (2006.01)

(52) U.S. Cl.
CPC .................. *A61B 8/54* (2013.01); *A61B 8/14* (2013.01); *A61B 8/4488* (2013.01); *A61B 8/5207* (2013.01)

(58) Field of Classification Search
CPC .. A61B 8/54; A61B 8/14; A61B 8/448; A61B 8/5207; A61B 8/4488; G01S 7/52085; G01S 15/8915
See application file for complete search history.

(56) References Cited

U.S. PATENT DOCUMENTS 5,123,415 A    6/1992  Daigle
5,148,810 A *  9/1992  Maslak ............... G01S 15/8927
                                                    600/447

(Continued)

FOREIGN PATENT DOCUMENTS

JP    H1-037146 B2    8/1989
JP    H09-192130 A    7/1997

(Continued)

OTHER PUBLICATIONS

JPO, Office Action for the corresponding Japanese patent application No. 2019-029803, dated May 24, 2022, with English translation.

*Primary Examiner* — Oommen Jacob
*Assistant Examiner* — Nyrobi Celestine
(74) *Attorney, Agent, or Firm* — Lucas & Mercanti, LLP

(57) ABSTRACT

An ultrasound diagnostic apparatus transmits ultrasound toward a subject by driving an ultrasound probe in which multiple transducers are arranged in an array, receives a reception signal that is based on waves reflected within the subject from the ultrasound probe, and generates an ultrasound image. The ultrasound diagnostic apparatus includes: a scan control section that sets scan conditions so that trapezoidal scanning is performed by the ultrasound probe; and a transmission section that controls driving of the ultrasound probe based on the scan conditions. The scan control section sets the scan conditions so that the inter-acoustic line angles in or around the center of the ultrasound probe are smaller than the inter-acoustic line angles near the edges when viewed along the scan direction.

14 Claims, 11 Drawing Sheets

(56) References Cited

U.S. PATENT DOCUMENTS

| | | | |
|---|---|---|---|
| 6,503,199 B1 * | 1/2003 | Lennon | G01S 7/52085 128/916 |
| 9,151,841 B2 * | 10/2015 | Lee | A61B 8/5253 |
| 2008/0064958 A1 * | 3/2008 | Ahn | G01S 15/8909 600/447 |
| 2009/0306511 A1 * | 12/2009 | Yamagata | A61B 8/0841 600/447 |
| 2012/0095342 A1 * | 4/2012 | Lee | G01S 7/52085 600/447 |
| 2014/0051984 A1 * | 2/2014 | Berger | A61B 8/467 600/424 |
| 2018/0085096 A1 * | 3/2018 | Brandl | A61B 8/469 |
| 2019/0201110 A1 * | 7/2019 | Kuenen | A61B 34/20 |
| 2019/0310367 A1 * | 10/2019 | Olsson | G01S 15/8918 |

FOREIGN PATENT DOCUMENTS

| | | | | |
|---|---|---|---|---|
| JP | 3135942 B2 | 2/2001 | | |
| JP | 2009-039232 A | 2/2009 | | |
| WO | WO-2014021105 A1 * | 2/2014 | | A61B 8/5253 |

* cited by examiner

ULTRASOUND DIAGNOSTIC TECHNIQUE FOR SETTING VIRTUAL ORIGINS OF ACOUSTIC LINES FOR TRAPEZOIDAL SCANNING

CROSS REFERENCE TO RELATED APPLICATIONS

The entire disclosure of Japanese Patent Application No. 2019-029803 filed on Feb. 21, 2019 is incorporated herein by reference in its entirety.

BACKGROUND

Technological Field

The present invention relates to an ultrasound diagnostic apparatus, an ultrasound diagnostic method, and a program, particularly to a technique useful for trapezoidal scanning that yields a wide-field view image.

Description of Related Art

Conventionally, as one of medical image diagnostic apparatuses, an ultrasound diagnostic apparatus is known which emits ultrasound toward a subject, receives reflected waves and subjects the reception signal to predetermined signal processing, thereby visualizing shapes, properties, or dynamics inside the subject in ultrasound images. The ultrasonic diagnostic apparatus can produce ultrasonic images through a simple operation of placing an ultrasound probe on the body surface or inserting it into the body, and is therefore safe and gives less damage on the subject.

An electronic scanning ultrasonic diagnostic apparatus uses, for example, the phased array technology that uses an ultrasound probe (so-called array probe) in which multiple transducers are arranged in an array and the timing when each transducer is driven is electronically changed so that the beam direction of the ultrasound and the shape of the ultrasound surface can be controlled. In the electronic scanning method, a transducer group consisting of multiple continuous transducers is sequentially driven, shifting in the direction along which transducers are aligned, which allows a diagnosis subject to be scanned in the direction along which transducers are aligned (hereinafter referred to as "scan direction").

Taking an example of electronic scanning method, trapezoidal scanning that can expand the diagnostic region by changing the beam direction of ultrasound has been put into practical use (see, for example, Patent Literature 1 (Japanese Examined Patent Application Publication No. H1-37146) and Patent Literature 2 (Japanese Patent No. 3135942)).

Patent Literature 1 discloses a method in which, as shown in FIGS. 1A and 1B, virtual origin VO is set on the back side of transducer 231 (opposite side of transducer side S), and transducer 231 is driven so that ultrasound acoustic line AL passes through one virtual origin VO and a region expanding in a trapezoidal shape is scanned (hereinafter referred to as "virtual origin method"). As shown in FIGS. 2A and 2B, Patent Literature 2 discloses a technique, which is related to trapezoidal scanning using the virtual origin method, for controlling scanning so that angle Δθ between acoustic lines AL of adjacent ultrasound beams (hereinafter referred to as "inter-acoustic line angle Δθ") becomes equal.

Incidentally, in ultrasonic diagnosis, the center of the scan region is region of interest ROI (see FIGS. 1A and 2A). However, in the case where the scan conditions in which acoustic line AL passes through virtual origin VO are set as in the virtual origin method disclosed in Patent Literatures 1 and 2, inter-acoustic line angle Δθ of region of interest ROI becomes wide (acoustic line density decreases), which lowers the image quality of region of interest ROI.

SUMMARY

An object of the present invention is to provide an ultrasound diagnostic apparatus, an ultrasound diagnostic method, and a computer-readable recording medium that can secure a wide field of view and improve the image quality at the center of the image.

To achieve at least one of the abovementioned objects, according to an aspect of the present invention, an ultrasound diagnostic apparatus reflecting one aspect of the present invention is an ultrasound diagnostic apparatus that transmits ultrasound toward a subject by driving an ultrasound probe in which a plurality of transducers are arranged in an array, receives a reception signal that is based on waves reflected within the subject from the ultrasound probe, and generates an ultrasound image, the ultrasound diagnostic apparatus comprising:

a hardware processor that sets a scan condition so that trapezoidal scanning is performed by the ultrasound probe; and a transmission section that controls driving of the ultrasound probe based on the scan condition, wherein when an angle between adjacent acoustic lines is defined as an inter-acoustic line angle, the hardware processor sets the scan condition so that the inter-acoustic line angles in or around the center of the ultrasound probe are smaller than the inter-acoustic line angles near the edges when viewed along the scan direction.

To achieve at least one of the abovementioned objects, according to another aspect of the present invention, an ultrasound diagnostic apparatus reflecting one aspect of the present invention is an ultrasound diagnostic apparatus that transmits ultrasound toward a subject by driving an ultrasound probe in which a plurality of transducers are arranged in an array, receives a reception signal that is based on waves reflected within the subject from the ultrasound probe, and generates an ultrasound image, the ultrasound diagnostic apparatus comprising:

a hardware processor that sets a scan condition so that trapezoidal scanning is performed by the ultrasound probe; and a transmission section that controls driving of the ultrasound probe based on the scan condition, wherein when a point where the normal line of a transducer surface in the center of the ultrasound probe when viewed along the scan direction and the acoustic line of the ultrasound intersect is defined as a virtual origin, the hardware processor sets the scan condition so that the virtual origins of the acoustic lines near the edges of the ultrasound probe are closer to the transducer than the virtual origins of the acoustic lines in or around the center.

To achieve at least one of the abovementioned objects, according to another aspect of the present invention, an ultrasound diagnostic method reflecting one aspect of the present invention is an ultrasound diagnostic method that involves transmitting ultrasound toward a subject by driving an ultrasound probe in which a plurality of transducers are arranged in an array, receiving a reception signal that is based on waves reflected within the subject from the ultrasound probe, and generating an ultrasound image, the ultrasound diagnostic method comprising:

setting a scan condition so that trapezoidal scanning is performed by the ultrasound probe; and controlling driving of the ultrasound probe based on the scan condition, wherein when an angle between adjacent acoustic lines is defined as an inter-acoustic line angle, in setting the scan condition, the scan condition is set so that the inter-acoustic line angles in or around the center of the ultrasound probe are smaller than the inter-acoustic line angles near the edges when viewed along the scan direction.

To achieve at least one of the abovementioned objects, according to another aspect of the present invention, a recording medium reflecting one aspect of the present invention is a non-transitory computer-readable recording medium storing a program causing a computer of an ultrasound diagnostic apparatus to execute a predetermined process, the ultrasound diagnostic apparatus transmitting ultrasound toward a subject by driving an ultrasound probe in which a plurality of transducers are arranged in an array, receiving a reception signal that is based on waves reflected within the subject from the ultrasound probe, and generating an ultrasound image, the predetermined process comprising:

setting a scan condition so that trapezoidal scanning is performed by the ultrasound probe; and controlling driving of the ultrasound probe based on the scan condition, wherein when an angle between adjacent acoustic lines is defined as an inter-acoustic line angle, in setting the scan condition, the scan condition is set so that the inter-acoustic line angles in or around the center of the ultrasound probe when viewed along the scan direction are smaller than the inter-acoustic line angles near the edges when viewed along the scan direction.

BRIEF DESCRIPTION OF DRAWINGS

The present invention will become more fully understood from the detailed description given hereinbelow and the appended drawings which are given by way of illustration only, and thus are not intended as a definition of the limits of the present invention, and wherein.

DETAILED DESCRIPTION OF EMBODIMENTS

Hereinafter, one or more embodiments of the present invention will be described with reference to the drawings. However, the scope of the invention is not limited to the disclosed embodiments.

Figure 3:
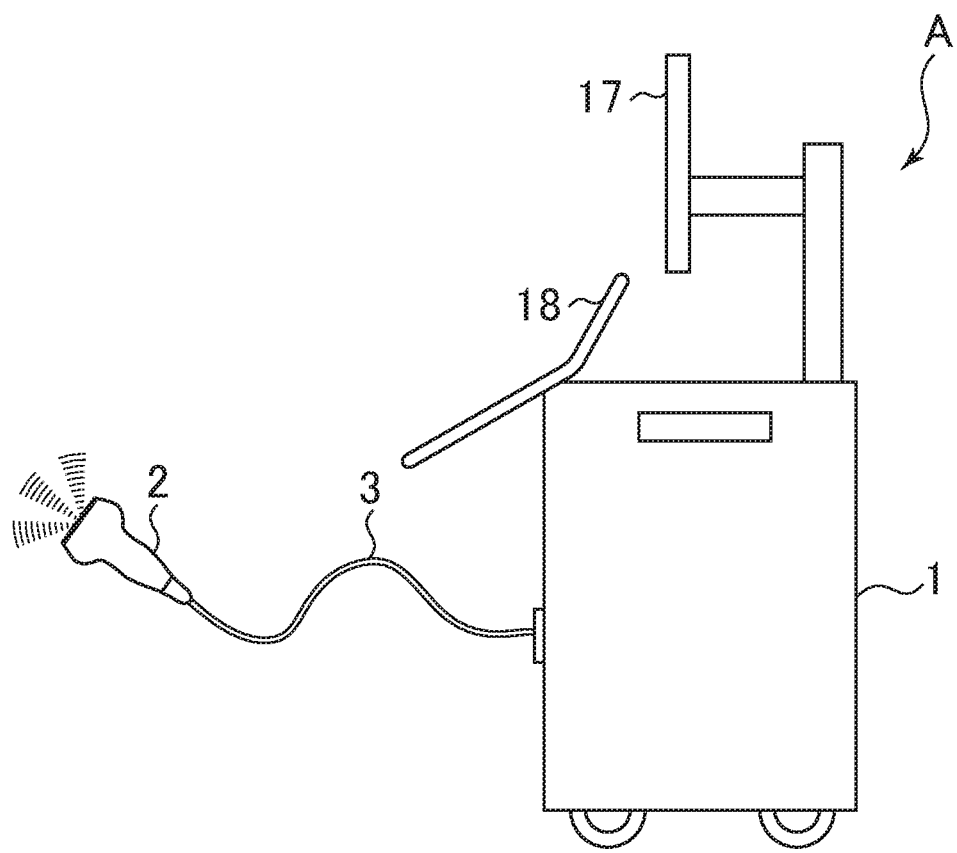
FIG. 3 is a diagram showing the appearance of an ultrasound diagnostic apparatus according to an embodiment.
Figure 4:
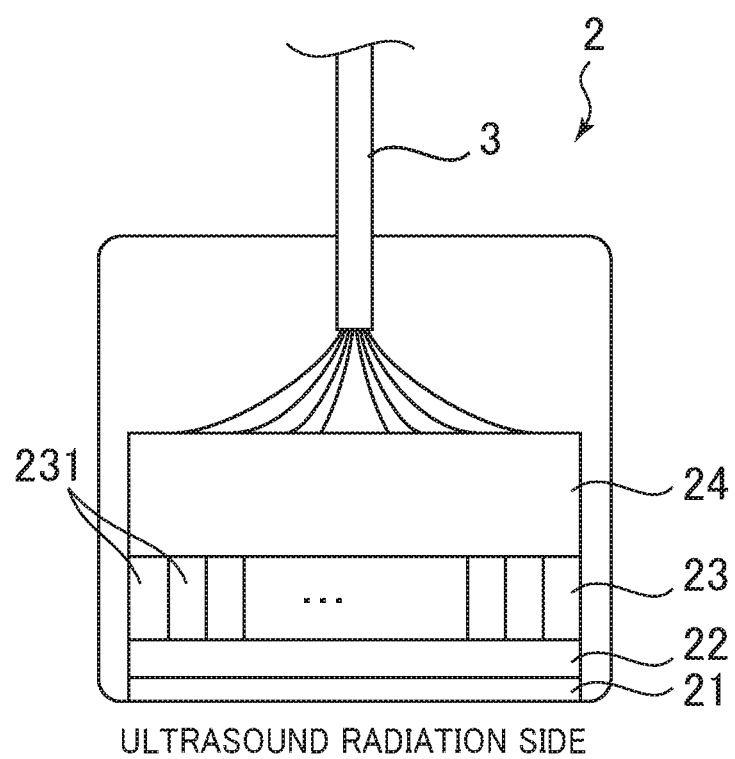
FIG. 4 is a diagram showing the configuration of an ultrasound probe.
Figure 5:
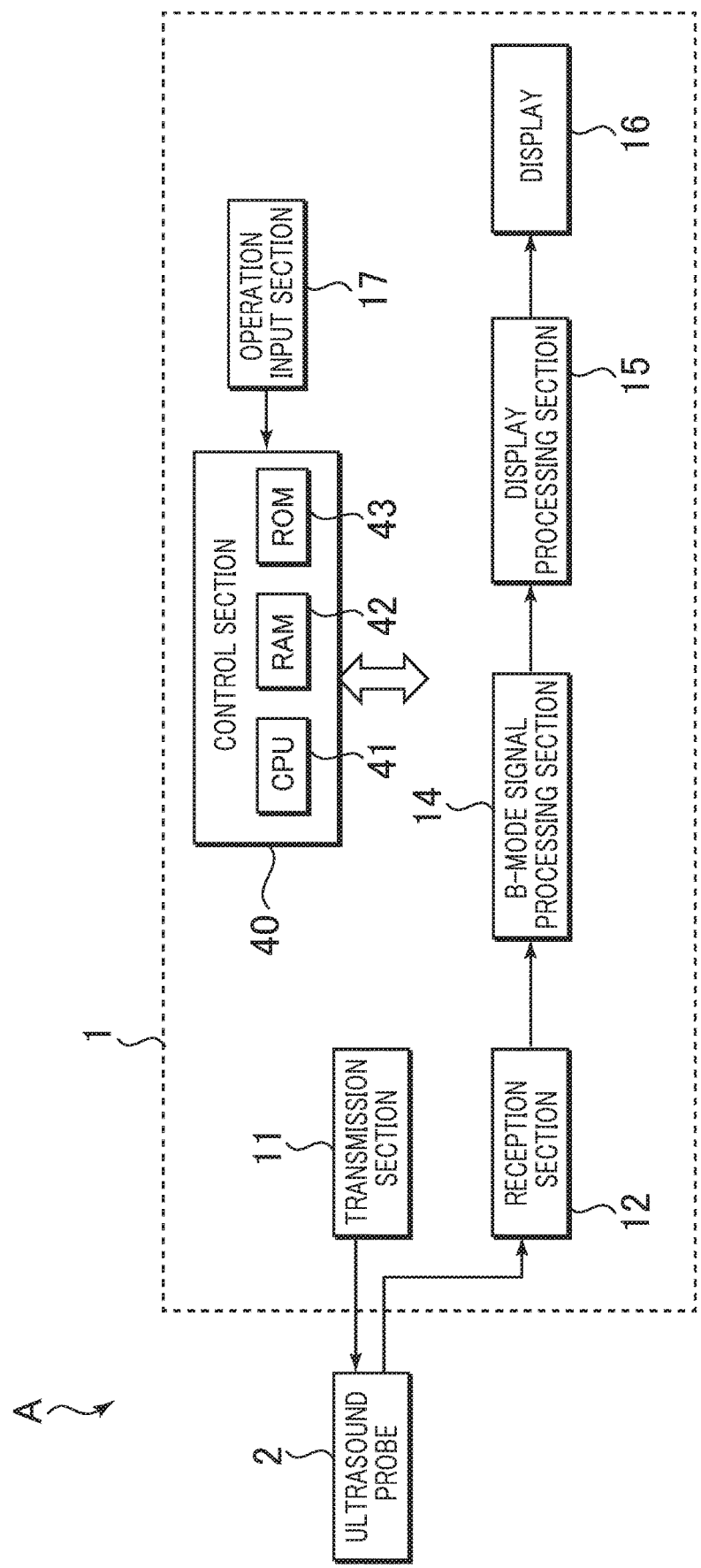
FIG. 5 is a block diagram showing the main part of the control system of an ultrasound diagnostic apparatus.

FIG. 3 is a diagram showing the appearance of ultrasound diagnostic apparatus A according to one embodiment of the present invention. FIG. 4 is a diagram showing the configuration of ultrasound probe 2. FIG. 5 is a block diagram showing the main part of the control system of ultrasound diagnostic apparatus A.

As shown in FIG. 3, ultrasound diagnostic apparatus A includes ultrasound diagnostic apparatus body 1 and ultrasound probe 2. Ultrasound diagnostic apparatus body 1 is connected to ultrasound probe 2 via cable 3. Note that ultrasound probe 2 may be connected to ultrasound diagnostic apparatus body 1 by wireless communication.

Ultrasound diagnostic apparatus A is used for visualizing the shape, properties, or dynamics in a subject in an ultrasound image and performing image diagnosis. Ultrasound diagnostic apparatus A has, as a display mode, a B mode in which only B-mode images are displayed. Note that ultrasound diagnostic apparatus A may have a color flow mapping (CFM) mode in which CFM images obtained by the color Doppler method superimposed on B-mode images are displayed.

For ultrasound diagnostic apparatus A, scan conditions can be set according to the type of ultrasound probe 2 to be connected thereto. For example, when a linear probe is used as ultrasound probe 2, ultrasound diagnostic apparatus A can switch between normal linear scanning that produces rectangular images and trapezoidal scanning that provides wider diagnostic areas than the linear scanning. Trapezoidal scanning using a linear probe provides a larger diagnostic area compared to linear scanning.

Ultrasound probe 2 transmits ultrasound to the subject, receives an ultrasonic echo reflected by the subject, converts it to a received signal, and transmits it to ultrasound diagnostic apparatus body 1. Ultrasound probe 2 is a probe compatible with the electronic scanning method, and can be, for example, a linear probe, a convex probe, or a sector probe. In this embodiment, the case where a linear probe is used as ultrasound probe 2 will be described.

As shown in FIG. 4, ultrasound probe 2 has acoustic lens 21, acoustic matching layer 22, transducer array 23, and backing material 24 in order from the side from which ultrasound is radiated. Note that a protective layer may be disposed on the surface (ultrasound radiation surface) of acoustic lens 21.

Acoustic lens 21 is a lens that converges ultrasound in the slice direction, and has, for example, a semi-cylindrical shape that is humped in the center when viewed along the slice direction.

Acoustic matching layer 22 is an intermediate material for efficiently allowing ultrasound to enter the subject, and matches the acoustic impedance of transducer 231 and the subject.

Transducer array 23 includes multiple strip-shaped transducers 231 aligned in the scan direction. Transducer array 23 may be a 1D array in which transducers 231 are arranged in a single row, or may be a 2D array in which transducers 231 are arranged in multiple rows.

Backing material 24 attenuates unnecessary vibration generated in transducer array 23.

With ultrasound probe 2, the beam profile of ultrasound that converges in the slice direction is obtained. Sequentially switching transducers 231 to be driven along the scan direction can converge ultrasound along the scan direction (so-called electronic focus).

Ultrasound diagnostic apparatus body 1 visualizes the internal state of the subject as an ultrasonic image, using the reception signal from ultrasound probe 2. As shown in FIG. 5, ultrasound diagnostic apparatus body 1 includes transmission section 11, reception section 12, B-mode signal processing section 14, display processing section 15, display 16, operation input section 17, and control section 40.

Transmission section 11, reception section 12, B-mode signal processing section 14, and display processing section 15 are each composed of, for example, at least one dedicated hardware (electronic circuit) appropriate for each process, such as a digital signal processor (DSP), an application specific integrated circuit (ASIC), or a programmable logic device (PLD).

Control section 40 includes central processing unit (CPU) 41 as an arithmetic/control apparatus, random access memory (RAM) 42 as a main storage apparatus, and read only memory (ROM) 43. ROM 43 stores basic programs and basic setting data. CPU 41 reads a program appropriate for the content of processing from ROM 43, expands it in RAM 42, and executes the expanded program, whereby the operations of the functional blocks (transmission section 11, reception section 12, B-mode signal processing section 14, display processing section 15, and display 16) of ultrasound diagnostic apparatus body 1 are centrally controlled.

In this embodiment, the function of each functional block is implemented when the hardware apparatus constituting the functional block cooperate with control section 40. Note that a part or all of the functions of each functional block may be implemented when control section 40 executes the program, and each functional block may have a configuration with which programs can be executed.

In this embodiment, control section 40 functions as a scan control section that sets scan conditions so that a predetermined scan operation is performed by ultrasound probe 2. The scan conditions include, for example, acoustic line angle θ of ultrasound to be transmitted and received. Acoustic line angle θ is the angle formed between acoustic line AL and normal line NV of transducer surface S. Acoustic line AL is the center line of each beam, and normal line NV is a line passing through beam starting point L described below.

Acoustic line angle θ is set for each beam starting point L. Beam starting point L is a point where ultrasound acoustic line AL and transducer surface S intersect. Position PL of beam starting point L (hereinafter referred to as beam starting point position PL) is expressed, for example, by a distance with a sign (±) with reference to the center of transducer array 23 when viewed along the scan direction. In the case of linear scanning, acoustic line angle θ is 0° regardless of beam starting point L. Meanwhile, in the case of trapezoidal scanning, acoustic line angle θ is set so that acoustic line AL is deflected by normal line NV.

Here, when a point where normal line NV of transducer surface S and acoustic line AL in the center of ultrasound probe 2 when viewed along the scan direction intersect is defined as virtual origin VO, the relationship expressed by Formula (1) below is established between position PO of virtual origin VO (hereinafter referred to as "virtual origin position PO"), beam starting point position PL, and acoustic line angle θ. Virtual origin position PO is represented by a distance from intersection point O between transducer surface S and normal line NV.

$$\theta = \arctan(PL/PO) \qquad (1)$$

In other words, the scan conditions may include virtual origin position PO instead of acoustic line angle θ.

Transmission section 11 generates a transmission signal (drive signal) in accordance with an instruction from control section 40 and outputs it to ultrasound probe 2. To be specific, transmission section 11 controls the operation of ultrasound probe 2 according to the scan condition set by control section 40. Although not shown, transmission section 11 includes, for example, a clock generation circuit, a pulse generation circuit, a pulse width setting section, and a delay circuit.

The clock generation circuit generates a clock signal that determines the transmission timing and transmission frequency of the pulse signal. The pulse generation circuit generates a bipolar rectangular wave pulse having a preset voltage amplitude at a predetermined cycle. The pulse width setting section sets the pulse width of the rectangular wave pulse output from the pulse generation circuit. The rectangular wave pulse generated by the pulse generation circuit is separated into different wiring paths for each transducer 231 of ultrasound probe 2 before or after being input to the pulse width setting section. The delay circuit delays the generated rectangular wave pulse according to the drive timing of each transducer 231 and outputs the delayed pulse to ultrasound probe 2.

Controlling the drive timing of transducer 231 allows multiple types of ultrasound transmitted at one scan to have different acoustic line angles θ, thereby achieving trapezoidal scanning.

Reception section 12 receives a reception signal from ultrasound probe 2 in accordance with an instruction from control section 40 and outputs it to B-mode signal processing section 14. Although not shown, reception section 12 includes, for example, an amplifier, an A/D conversion circuit, and a phasing addition circuit.

The amplifier amplifies the reception signal corresponding to the ultrasound received by each transducer 231 of ultrasound probe 2, with a preset predetermined amplification factor. The A/D conversion circuit converts the amplified reception signal into digital data at a predetermined sampling frequency. For the A/D converted reception signal, the phasing addition circuit adjusts the time phase by giving a delay time to each wiring path corresponding to transducer 231 and adds these (phasing addition).

B-mode signal processing section 14 performs an envelope detection process, a logarithmic compression process, and the like on the reception data for B-mode images from reception section 12, according to instructions from control section 40 to adjust the dynamic range and gain for luminance conversion, thereby generating B-mode image data.

Display processing section 15 converts the image data generated in B-mode signal processing section 14 into a display signal compatible with display 16 according to an instruction from control section 40 and outputs the display signal so that B-mode images are displayed on display 16. Note that display processing section 15 includes a digital scan converter (DSC) that performs coordinate conversion and pixel interpolation according to the type of ultrasound probe 2.

Display 16 includes, for example, a liquid crystal display, an organic EL display, and a CRT display. Display 16 displays an image based on a display signal from display processing section 15 in accordance with an instruction from control section 40.

Operation input section 17 accepts input of information related to diagnosis, for example. Operation input section 17 includes, for example, an operation panel having multiple input switches, a keyboard, a mouse, and the like. The user can set the region of interest, the diagnostic region, the type of ultrasound probe 2, the scan mode (linear/trapezoid), and the like via operation input section 17.

Note that display 16 and/or operation input section 17 may be an external apparatus (for example, a tablet) communicably connected to ultrasound diagnostic apparatus body 1.

Figure 6A:
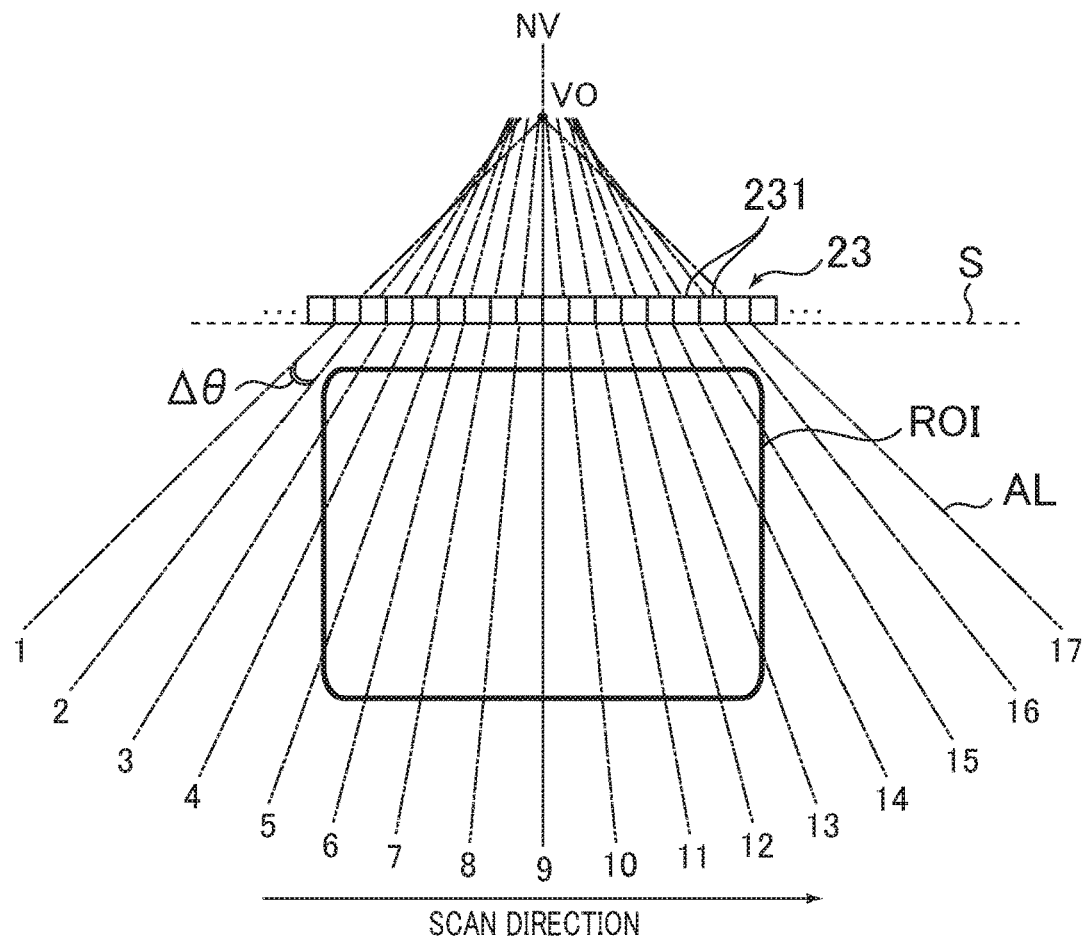
FIGS. 6A and 6B are diagrams showing examples of acoustic lines formed when trapezoidal scanning is performed with an ultrasound diagnostic apparatus.
Figure 6B:
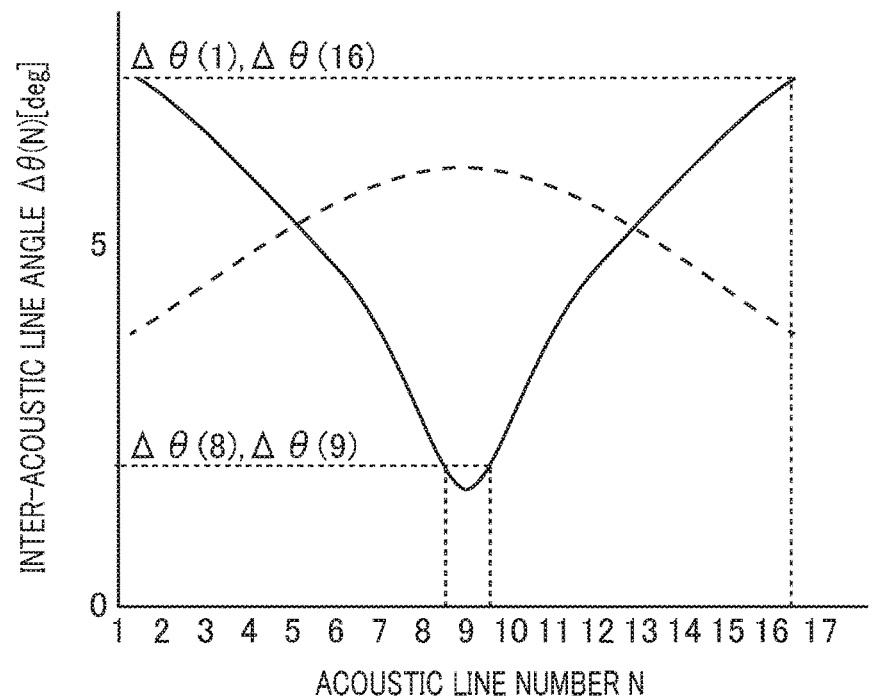
Figure 7A:
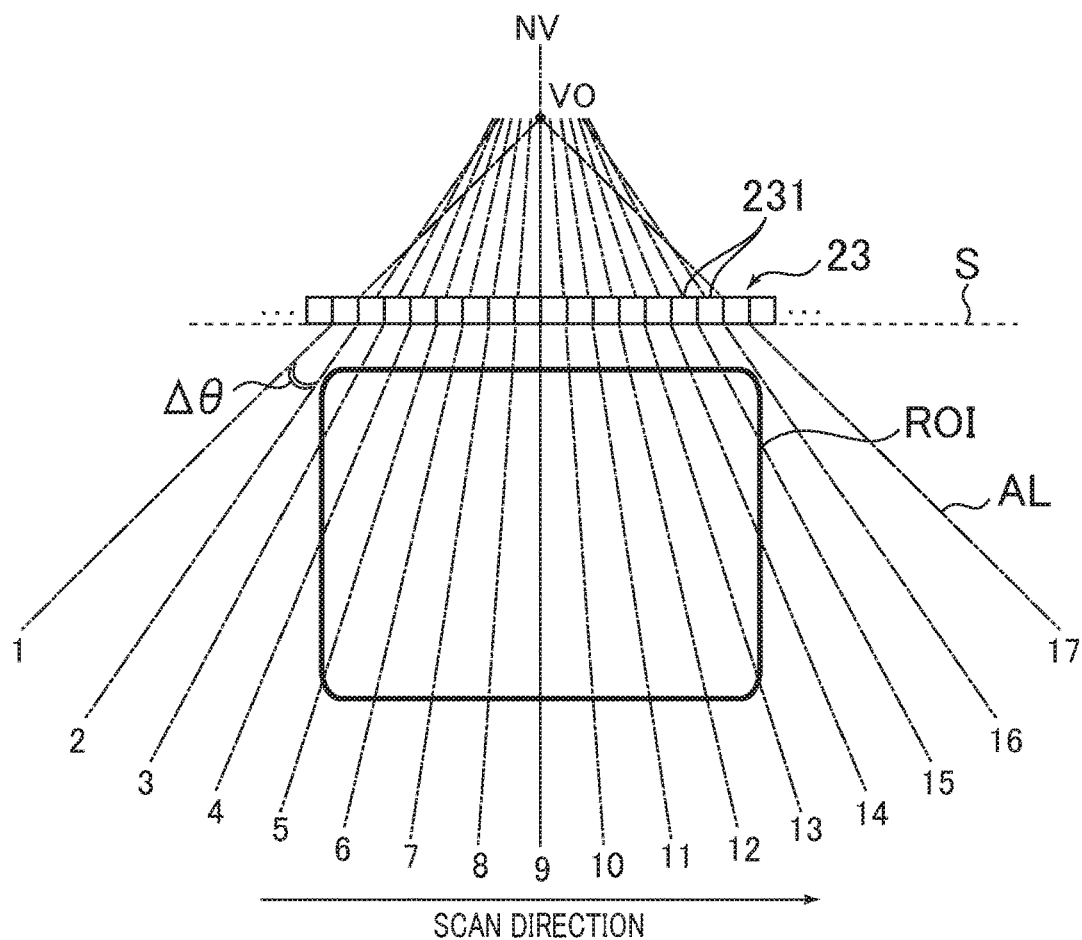
FIGS. 7A and 7B are diagrams showing other examples of acoustic lines formed when trapezoidal scanning is performed with an ultrasound diagnostic apparatus.
Figure 7B:
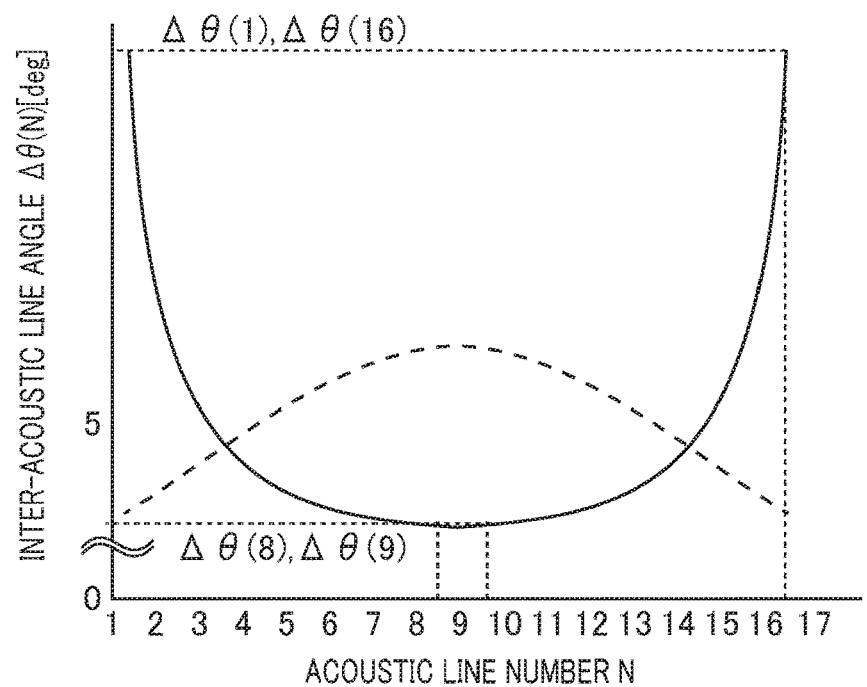
Figure 8:
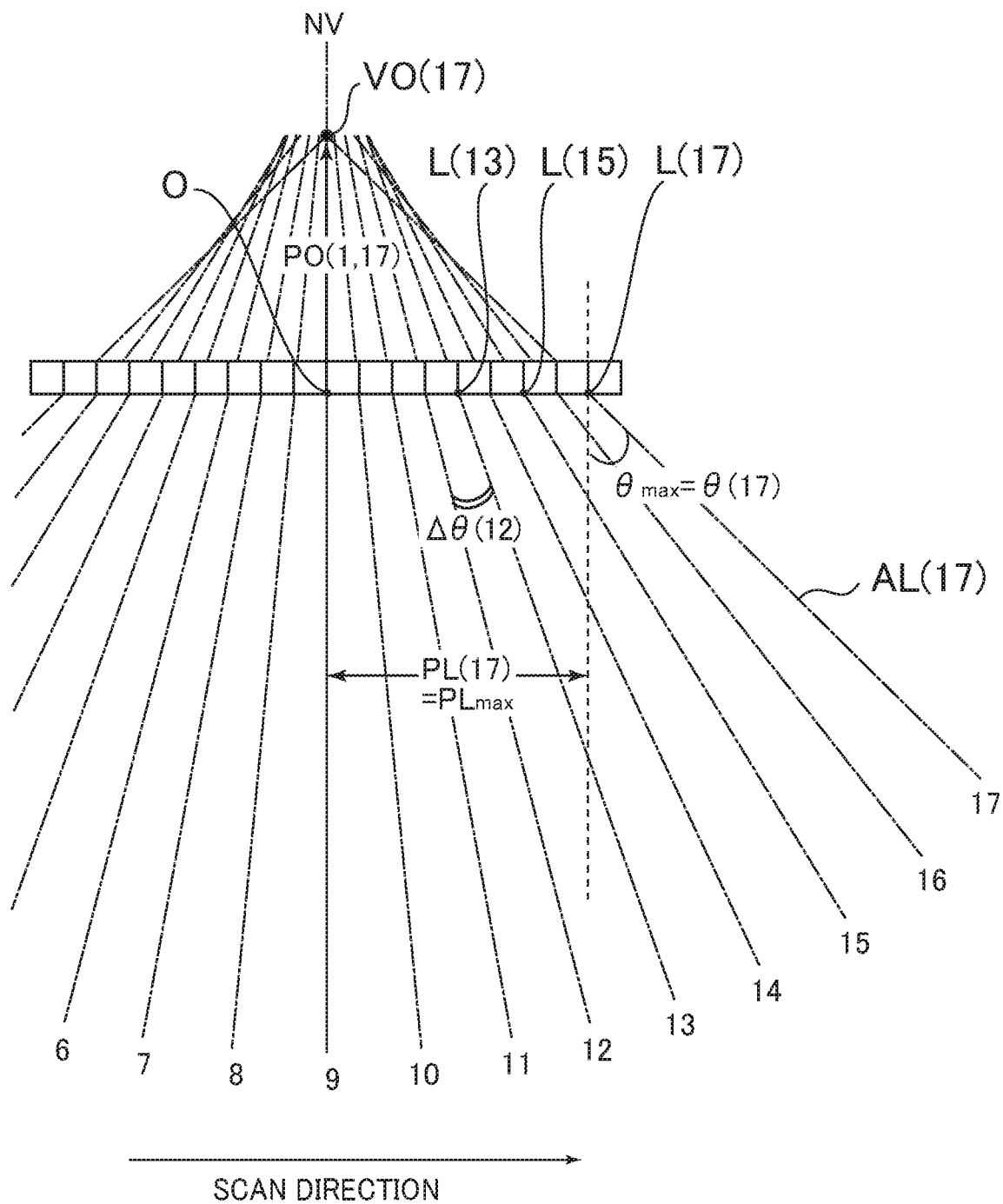
FIG. 8 is a diagram for explaining parameters defining acoustic lines.

FIGS. 6A and 6B are diagrams showing examples of acoustic lines AL formed when trapezoidal scanning is performed with ultrasound diagnostic apparatus A. FIGS. 7A and 7B are diagrams showing other examples of acoustic lines AL formed when trapezoidal scanning is performed with ultrasound diagnostic apparatus A. FIG. 8 is a diagram for explaining parameters defining acoustic lines AL.

As described above, acoustic line AL passes through the boundary between, of the transducer group driven by one time of transmission/reception of ultrasound, two transducers 231 in the center when viewed along the scan direction. FIGS. 6A and 7A show the case where the structure of transducer array 23 is simplified, and trapezoidal scanning is performed once by 17 times of transmission/reception of ultrasound, that is, the case where 17 acoustic lines AL are formed by one time of trapezoidal scanning.

Figure 1A:
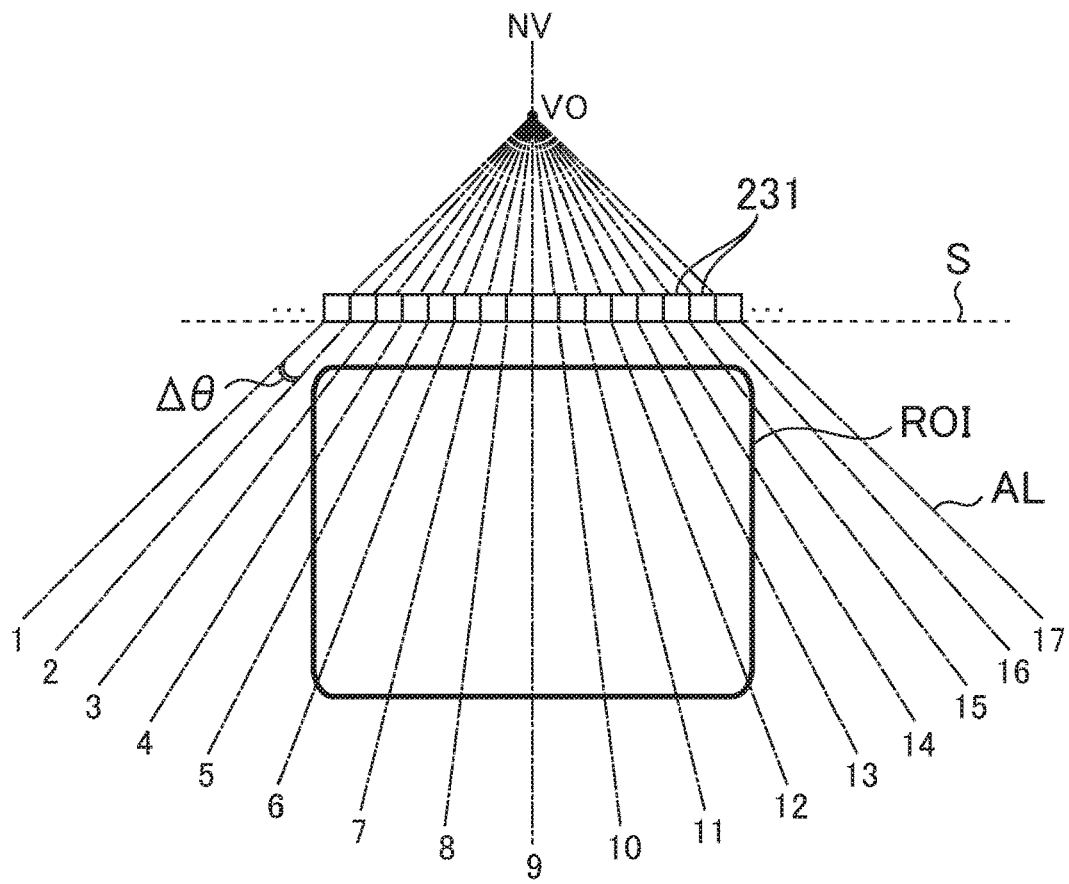
FIGS. 1A and 1B are diagrams showing examples of acoustic lines in conventional trapezoidal scanning.

In FIGS. 6B and 7B, inter-acoustic line angle $\Delta\theta$ obtained when acoustic lines AL shown in FIGS. 6A and 7A are formed is indicated by a solid line, and inter-acoustic line angle $\Delta\theta$ obtained when acoustic lines AL shown in FIG. 1A are formed is indicated by a dashed line.

The Nth (N=1 to 17) acoustic line AL from the left in FIGS. 6A and 7A will be hereinafter represented by "acoustic line AL (N)", and acoustic line angle $\theta$ of acoustic line AL (N), beam starting point L, virtual origin VO, beam starting point position PL, and virtual origin position PO will be represented by "acoustic line angle $\theta$ (N)", "beam starting point L (N)", "virtual origin VO (N)", "beam starting point position PL (N)", and virtual origin position PO (N), respectively. Inter-acoustic line angle $\Delta\theta$ between the adjacent acoustic lines AL (N) and AL (N+1) will be represented by "inter-acoustic line angle $\Delta\theta$ (N)".

As shown in FIGS. 6B and 7B, in this embodiment, inter-acoustic line angle $\Delta\theta$ (for example, inter-acoustic line angle $\Delta\theta$ (8) or $\Delta\theta$ (9)) in or around the center of ultrasound probe 2 is smaller than inter-acoustic line angle $\Delta\theta$ near the edges (for example, inter-acoustic line angle $\Delta\theta$ (1) or $\Delta\theta$ (16)) when viewed along the scan direction. In other words, when viewed along the scan direction, the scan conditions are set so that inter-acoustic line angles $\Delta\theta$ in or around the center of ultrasound probe 2 are smaller than inter-acoustic line angles $\Delta\theta$ near the edges. It can also be said that the scan conditions are set so that the closer the acoustic line AL is to the edge when viewed along the scan direction, the closer the virtual origin VO is to transducer surface S.

Figure 1B:
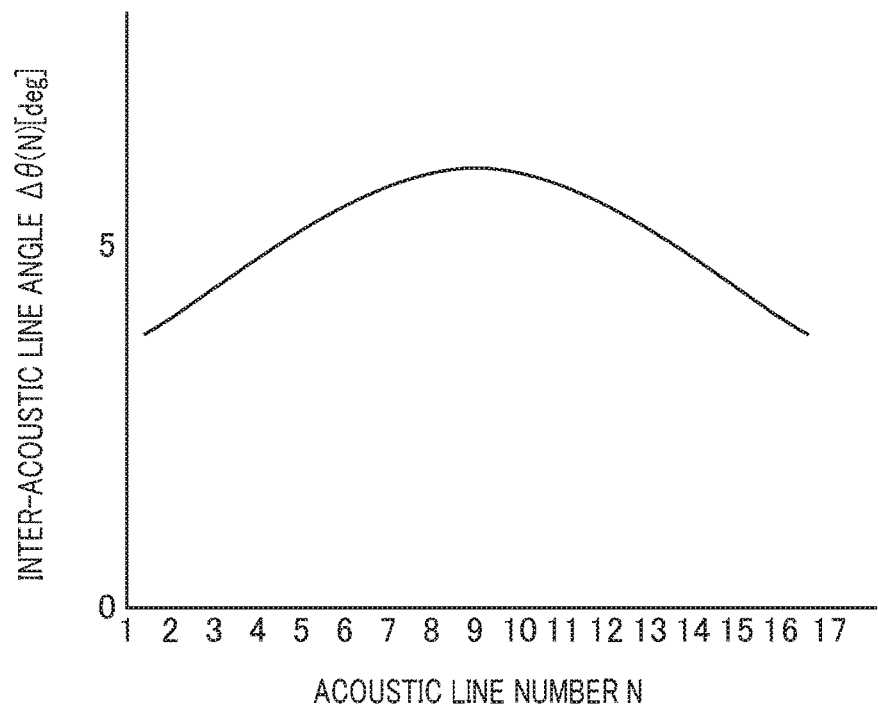
Figure 2A:
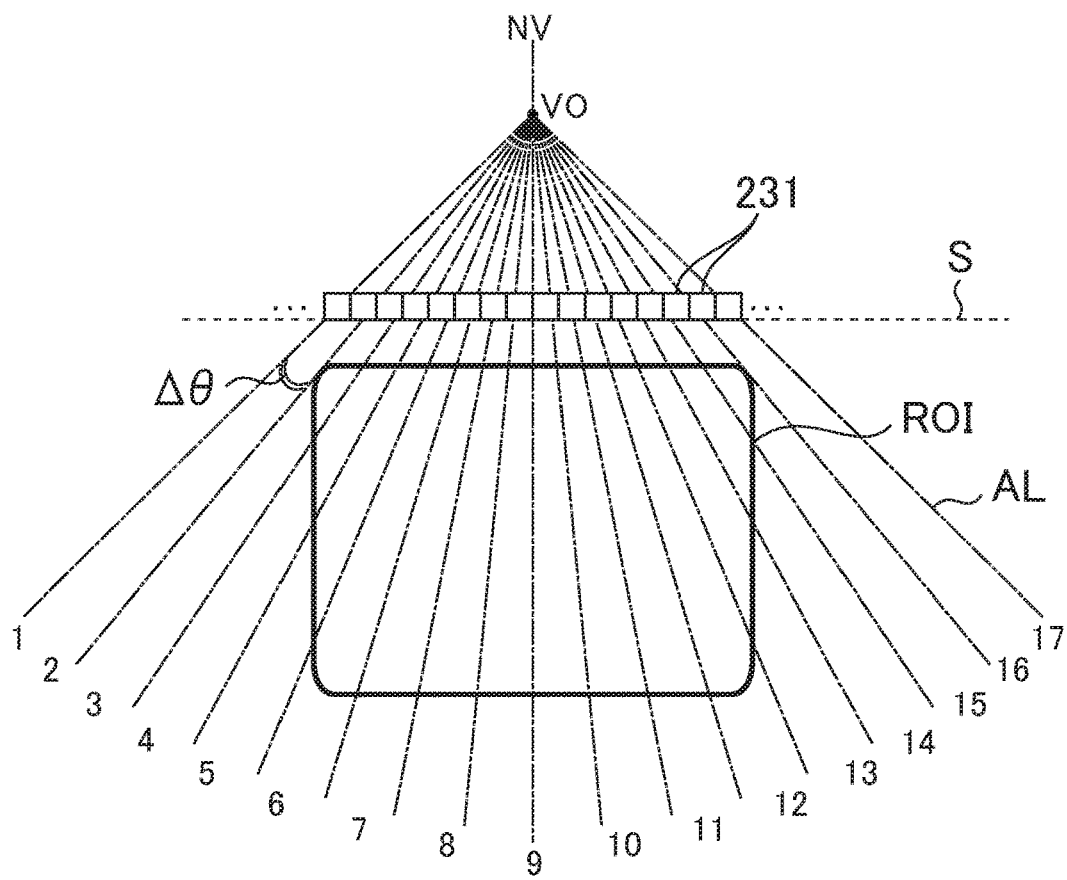
FIGS. 2A and 2B are diagrams showing other examples of acoustic lines in conventional trapezoidal scanning.
Figure 2B:
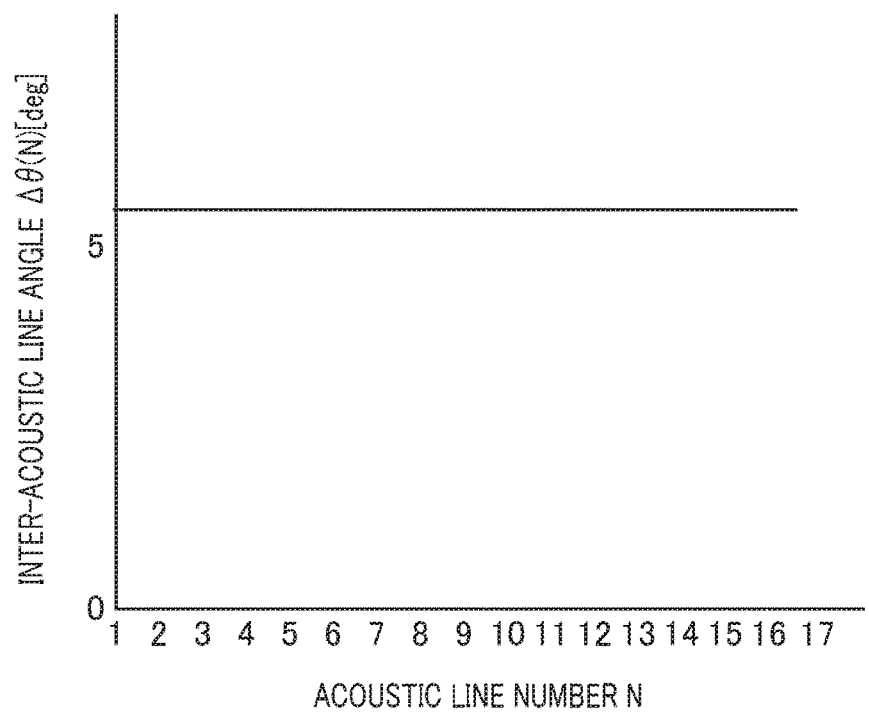

Hence, inter-acoustic line angle $\Delta\theta$ becomes smaller and the acoustic line density is increased toward the center when viewed along the scan direction of ultrasound probe 2. Accordingly, compared with the conventional virtual origin method (see FIGS. 1A and 1B) in which inter-acoustic line angle $\Delta\theta$ is larger toward the center of ultrasound probe 2, the image quality in the center of the region of interest ROI, which is to be diagnosed, is improved.

Acoustic lines AL are formed symmetrical about normal line NV passing through the center of transducer surface S, and inter-acoustic line angle $\Delta\theta$ increases monotonously from the center toward the edge when viewed along the scan direction of ultrasound probe 2, and becomes smaller toward the center and larger toward the edge when viewed along the scan direction of ultrasound probe 2. Thus, an ultrasound image with stable image quality can be obtained.

In the trapezoidal scanning using ultrasound of acoustic lines AL shown in FIGS. 6A and 6B, the change in inter-acoustic line angle $\Delta\theta$ in the center when viewed along the scan direction is steep. In this case, the image quality in the center of the image is improved, but the image quality steeply drops toward the edge, which may impair the visibility. In contrast, for acoustic lines AL shown in FIGS. 7A and 7B, the change in inter-acoustic line angle $\Delta\theta$ is gentle in the range of the fifth acoustic line AL (5) to the thirteenth acoustic line AL (13), but is steep in the range of acoustic lines AL (5 and 13) to the edge. As described above, it is made smaller toward the center and larger toward the edge when viewed along the scan direction of ultrasound probe 2; thus, an abrupt change in the image quality can be suppressed and an ultrasound image with stable image quality can be obtained. In particular, it is preferable that inter-acoustic line angle $\Delta\theta$ be set substantially equal for acoustic lines AL forming the region of interest ROI.

Figure 9:
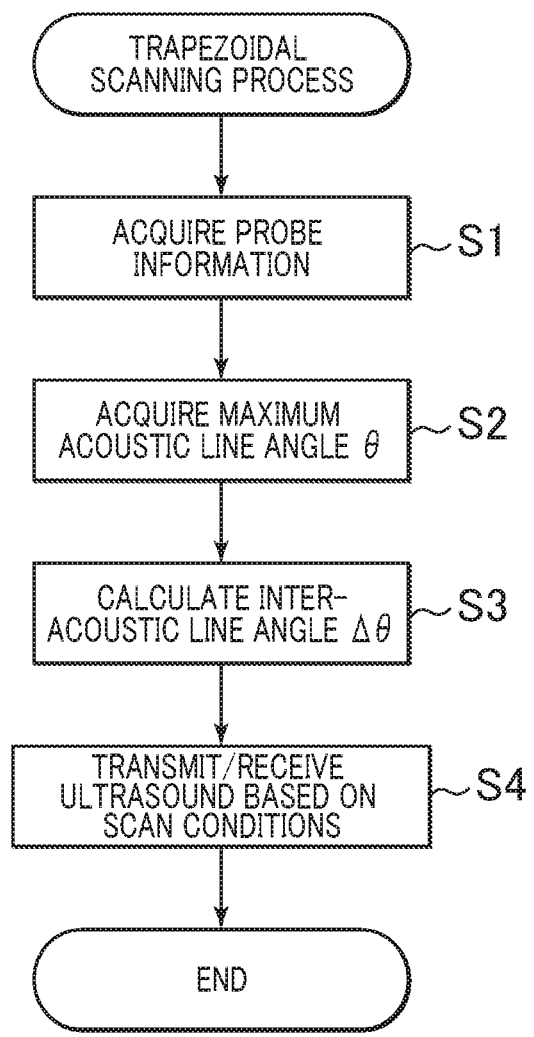
FIG. 9 is a flowchart showing an example of a trapezoidal scanning process.

FIG. 9 is a flowchart showing an example of a trapezoidal scanning process. This process is implemented, for example, when the trapezoidal scanning mode is selected and CPU 41 therefore executes a predetermined program stored in ROM 43 in ultrasound diagnostic apparatus A. For example, when the user selects the trapezoidal scanning mode via operation input section 17, a trapezoidal scanning process is started.

In Step S1 in FIG. 9, control section 40 acquires probe information related to ultrasound probe 2 connected to ultrasound diagnostic apparatus body 1. The probe information contains the type of ultrasound probe 2 and the configuration of transducer array 23 (for example, the number of transducers and the transducer size). The probe information is pre-stored in ROM 43, for example, and is appropriately read according to ultrasound probe 2 to be used. The probe information stored in ROM 43 may be updated by user's input operation on operation input section 17.

In Step S2, control section 40 acquires maximum acoustic line angle $\theta$max. As shown in FIG. 8, maximum acoustic line angle $\theta$max is acoustic line angle $\theta$ of the outermost acoustic line AL (acoustic line angle $\theta$ (17) of acoustic line AL (17) in FIG. 8). Maximum acoustic line angle $\theta$max is provided, for example, by a user input operation on operation input section 17.

In Step S3, control section 40 calculates acoustic line angle $\theta$ of each acoustic line AL based on the probe information and maximum acoustic line angle $\theta$max acquired in Steps S1 and S2. For the calculation of acoustic line angle $\theta$, a function is applied so that inter-acoustic line angle $\Delta\theta$ becomes small in the middle when viewed along the scan direction. A specific example of this function will be described later.

In Step S4, control section 40 transmits acoustic line angle $\theta$ calculated in Step S3, as a scan condition, to transmission section 11 and reception section 12, and causes them to perform trapezoidal scanning. In transmission section 11, delay control is performed based on the scan conditions and trapezoidal scanning by ultrasound probe 2 is executed.

Figure 10:
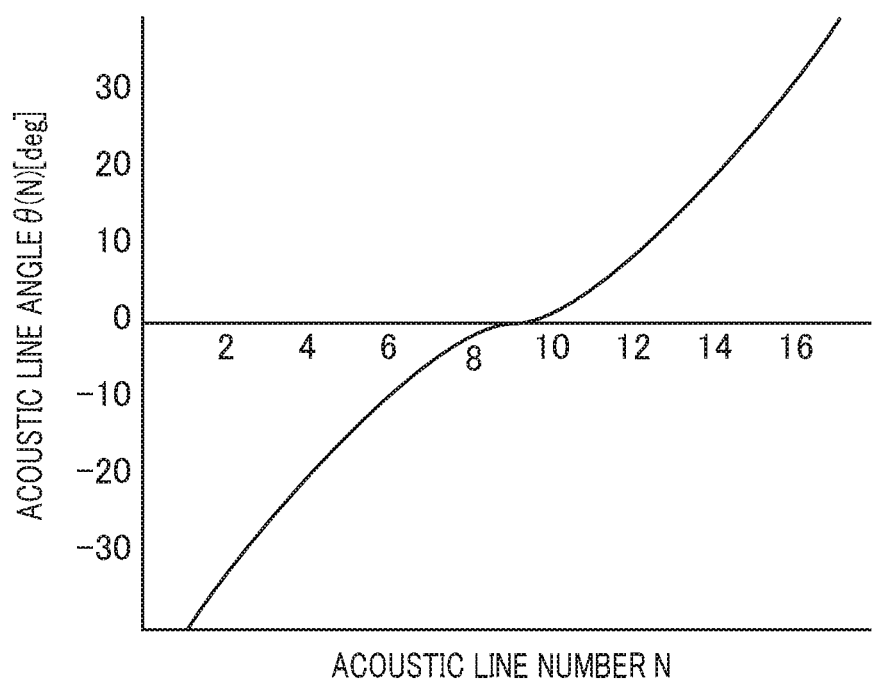
FIG. 10 is a diagram showing an example of a function used in calculation of an acoustic line angle in the trapezoidal scanning process (Step S3 in FIG. 9)
Figure 11:
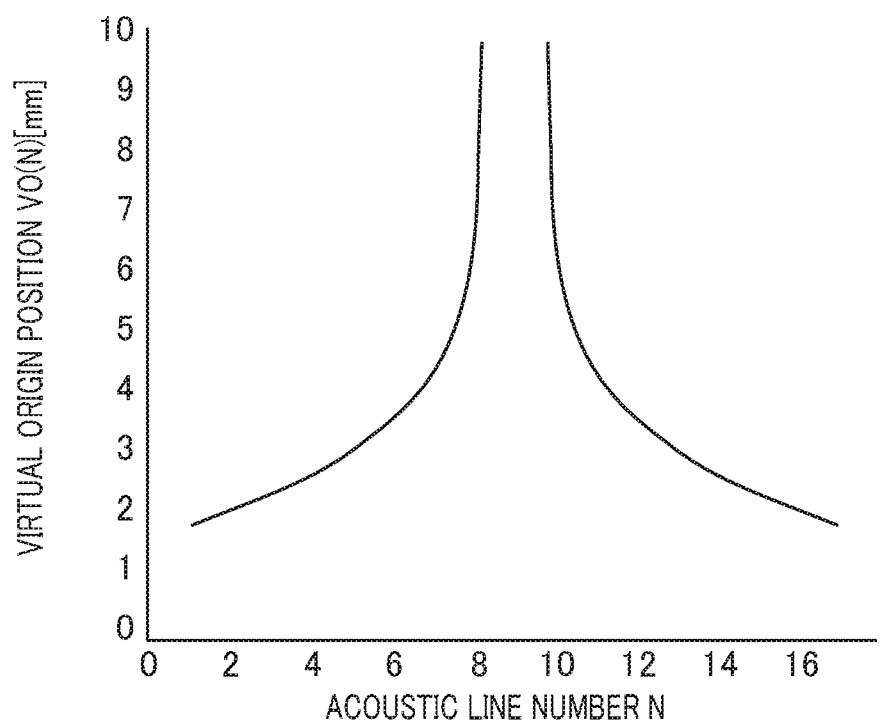
FIG. 11 is a diagram showing an example of a function used in calculation of an acoustic line angle in the trapezoidal scanning process (Step S3 in FIG. 9)

FIGS. 10 and 11 are diagrams showing an example of a function used in calculation of acoustic line angle θ in the trapezoidal scanning process (Step S3 in FIG. 9).

The functions shown in FIGS. 10 and 11 exhibit substantially the same characteristics. In FIG. 10, acoustic line angle θ is shown as a function of beam starting point position PL. In FIG. 11, virtual origin position PO is shown as a function of beam starting point position PL. To be specific, the function shown in FIG. 10 is expressed by Formula (2) below, and the function shown in FIG. 11 is expressed by Formula (3) below.

$$\theta = \text{sgn}(L) \times \beta \times |PL|^{\alpha} \quad (2)$$

$$PO = L/\tan\{\text{sgn}(L) \times \beta \times |PL|^{\alpha}\} \quad (3)$$

sgn(L): a sign of beam starting point

α, β: deflection angle variation coefficient

Here, deflection angle variation coefficients α and β are characteristic values for controlling inter-acoustic line angle Δθ, where α is a constant and the outermost beam starting point position PLmax (=PL (17)) on the positive side, and defining the corresponding acoustic line angle θmax (=θ (17)) determines β.

When acoustic line angle θ is determined according to Formula (2) or Formulas (1) and (3), inter-acoustic line angle Δθ reaches a minimum value in the center when viewed along the scan direction of ultrasound probe 2. In other words, for the function representing acoustic line angle θ or virtual origin position PO, such a function that inter-acoustic line angle Δθ reaches a minimum value in the center when viewed along the scan direction of ultrasound probe 2 is applied. In particular, as shown in FIGS. 6B and 7B, it is preferable that inter-acoustic line angle Δθ reach a minimum value in the center when viewed along the scan direction of ultrasound probe 2.

Through calculation of acoustic line angle θ using the functions shown in FIGS. 10 and 11, the scan conditions can be set as appropriate, which leads to flexibility according to the type of ultrasound probe 2 to be used.

Note that, in order to increase display accuracy and workability, these functions are preferably such that an algebraic solution exists in the coordinate transformation performed to generate an image to be displayed in display processing section 15.

As described above, ultrasound diagnostic apparatus A according to this embodiment transmits ultrasound toward a subject by driving ultrasound probe 2 in which multiple transducers 231 are arranged in an array, receives a reception signal that is based on waves reflected within the subject from ultrasound probe 2, and generates ultrasound images, and includes control section 40 (scan control section) that sets scan conditions so that trapezoidal scanning is performed by ultrasound probe 2, and transmission section 11 that controls driving of the ultrasound probe based on the scan conditions. When the angle between the adjacent acoustic lines AL is defined as inter-acoustic line angle Δθ, control section 40 sets scan conditions so that inter-acoustic line angles Δθ in or around the center when viewed along the scan direction of ultrasound probe 2 are smaller than inter-acoustic line angles Δθ near the edges.

In other words, ultrasound diagnostic apparatus A transmits ultrasound toward a subject by driving ultrasound probe 2 in which multiple transducers 231 are arranged in an array, receives a reception signal that is based on waves reflected within the subject from ultrasound probe 2, and generates ultrasound images, and includes control section 40 (scan control section) that sets scan conditions so that trapezoidal scanning is performed by ultrasound probe 2, and transmission section 11 that controls driving of the ultrasound probe based on the scan conditions. When a point where normal line NV of transducer surface S and acoustic line AL of ultrasound in the center of ultrasound probe 2 when viewed along the scan direction intersect is defined as virtual origin VO, control section 40 sets the scan conditions so that virtual origins VO of acoustic lines AL near the edges of ultrasound probe 2 are closer to transducer 231 than virtual origins VO of acoustic lines AL in or around the center.

As described above, an ultrasound diagnostic method according to this embodiment transmits ultrasound toward a subject by driving ultrasound probe 2 in which multiple transducers 231 are arranged in an array, receives a reception signal that is based on waves reflected within the subject from ultrasound probe 2, and generates ultrasound images, and includes a first step (Steps S1 to S3 in FIG. 9) in which scan conditions are set so that trapezoidal scanning is performed by ultrasound probe 2, and a second step (Step S4 in FIG. 9) in which driving of the ultrasound probe is controlled based on the scan conditions. When the angle between the adjacent acoustic lines AL is defined as inter-acoustic line angle Δθ, the first step sets scan conditions so that inter-acoustic line angles Δθ in or around the center when viewed along the scan direction of ultrasound probe 2 are smaller than inter-acoustic line angles Δθ near the edges when viewed along the scan direction.

A program according to this embodiment is a program that causes the computer of ultrasound diagnostic apparatus A to execute a predetermined process, ultrasound diagnostic apparatus A transmitting ultrasound toward a subject by driving ultrasound probe 2 in which multiple transducers 231 are arranged in an array, receiving a reception signal that is based on waves reflected within the subject from ultrasound probe 2, and generating ultrasound images. The predetermined process includes a first process (Steps S1 to S3 in FIG. 9) in which scan conditions are set so that trapezoidal scanning is performed by ultrasound probe 2, and a second process (Step S4 in FIG. 9) in which driving of the ultrasound probe is controlled based on the scan conditions. When the angle between the adjacent acoustic lines AL is defined as inter-acoustic line angle Δθ, the first process sets scan conditions so that inter-acoustic line angles Δθ in or around the center when viewed along the scan direction of ultrasound probe 2 are smaller than inter-acoustic line angles Δθ near the edges when viewed along the scan direction.

This program is provided via, for example, a computer-readable portable storage medium (including an optical disk, a magneto-optical disk, and a memory card) that stores the program. For example, this program can be downloaded from a server having the program via a network.

With ultrasound diagnostic apparatus A, the ultrasound diagnostic method, and the program according to the embodiment, a wide field of view can be ensured by trapezoidal scanning, and the acoustic line density is increased in or around the center when viewed along the scan direction of ultrasound probe 2, so that the image quality in or around the center of the image can be improved.

The invention made by the present inventor has been specifically described above based on the embodiment; however, the present invention is not limited to the above-described embodiment, and can be modified without departing from its scope.

For example, in the embodiment, acoustic lines AL are symmetrical about normal line NV passing through the center of transducer surface S; however, acoustic lines AL are not necessarily symmetrical.

For example, the case where acoustic line angle θ, which is a scan condition, is calculated by calculation using a function has been described in this embodiment; alternatively, the data of acoustic line angle θ preset according to the type of ultrasound probe 2 or the like may be held in control section 40. Aside from that, virtual origin position PO may be used as a scan condition.

Furthermore, ultrasound diagnostic apparatus A may include an image processing section that generates an ultrasonic image by spatially synthesizing multiple frames obtained by transmitting and receiving ultrasound obtained by deflecting each acoustic line AL by a certain angle (so-called spatial compound). Hence, the uniformity of the ultrasonic image can be improved.

Figure 12A:
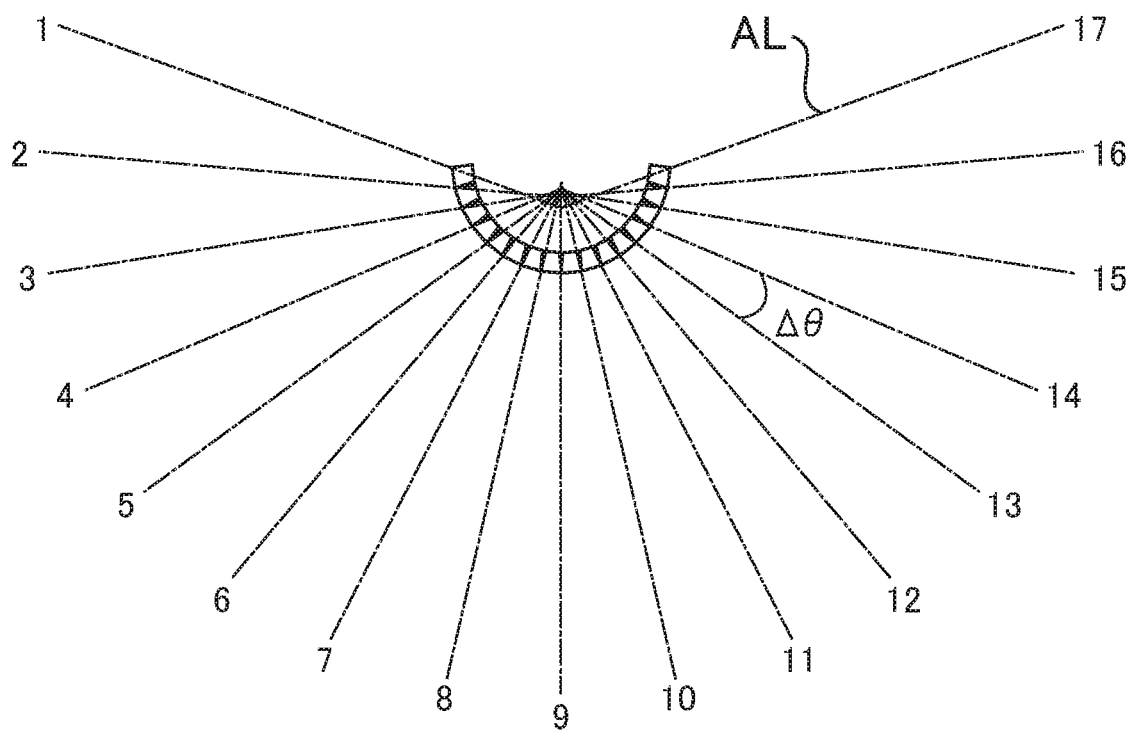
FIGS. 12A and 12B are diagrams showing examples of acoustic lines formed using a convex probe.
Figure 12B:
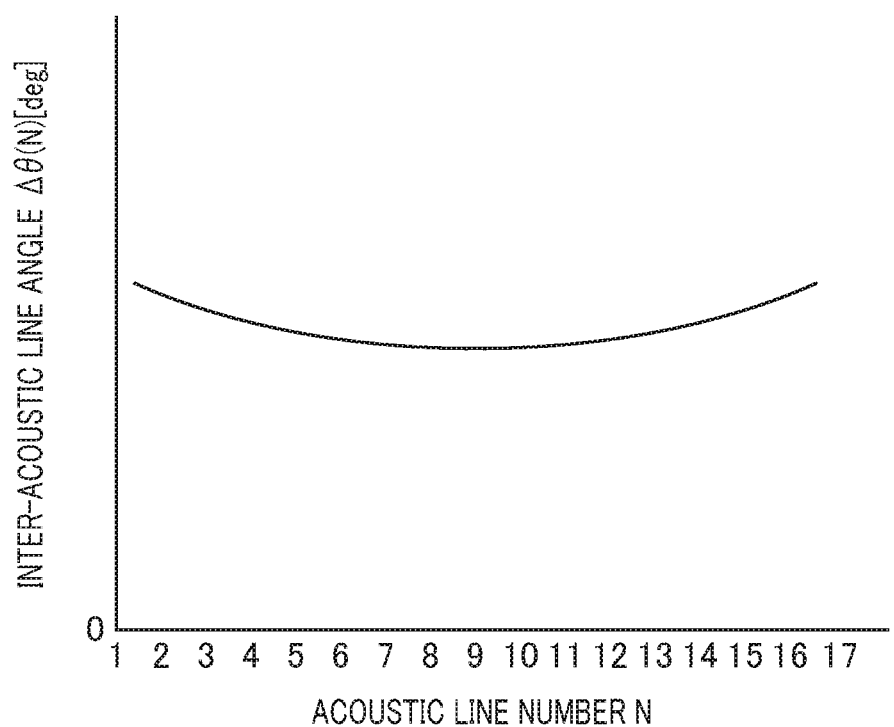

The case where a linear probe is used as ultrasound probe 2 has been described in the embodiment; alternatively, a convex probe may be used. FIGS. 12A and 12B are diagrams showing examples of acoustic lines AL formed using a convex probe. As shown in FIGS. 12A and 12B, also in this case, a wide field of view can be ensured by trapezoidal scanning, and the acoustic line density is increased in or around the center when viewed along the scan direction of ultrasound probe 2, so that the image quality in or around the center of the image can be improved.

Inter-acoustic line angle Δθ continuously changes smoothly in FIGS. 6B and 7B, but the shape representing the change in inter-acoustic line angle Δθ is not necessarily like this. For example, inter-acoustic line angle Δθ may change stepwise so that multiple inter-acoustic line angles Δθ that are continuous in the center of transducer surface S when viewed along the scan direction are the same.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasound diagnostic apparatus that transmits ultrasound toward a subject by driving an ultrasound probe in which a plurality of transducers are arranged in an array, receives a reception signal that is based on waves reflected within the subject from the ultrasound probe, and generates an ultrasound image, the ultrasound diagnostic apparatus comprising:
   a hardware processor that sets a scan condition so that trapezoidal scanning is performed by the ultrasound probe, wherein each acoustic line of a plurality of acoustic lines of the trapezoidal scanning has a different beam starting point where the each acoustic line and a transducer surface of the array of transducers intersect; and
   a transmission section that controls driving of the ultrasound probe based on the scan condition, wherein
   an angle between adjacent acoustic lines is defined as an inter-acoustic line angle,
   a point where the normal line of a transducer surface in the center of the ultrasound probe along the scan direction and the acoustic line of the ultrasound intersect is defined as a virtual origin,
   the hardware processor sets the scan condition so that the inter-acoustic line angles in or around the center of the ultrasound probe are smaller than the inter-acoustic line angles near the edges along the scan direction,
   the acoustic lines are symmetrical about a normal line passing through the center of the transducer surface of the ultrasound probe and the position of the virtual origin of a symmetric pair of the acoustic lines is different from the positions of the virtual origins of the other symmetric pairs of the acoustic lines, and
   the scan condition is set so that the virtual origins of the acoustic lines near the edges of the ultrasound probe are closer to the transducer than the virtual origins of the acoustic lines in or around the center.

2. The ultrasound diagnostic apparatus according to claim 1, wherein
   an angle between the normal line of the transducer surface of the ultrasound probe and an acoustic line of the ultrasound is defined as an acoustic line angle, and
   the acoustic line angle is represented by a function of the beam starting point position, the function being set so that the minimum inter-acoustic line angle is obtained in the center of the ultrasound probe along the scan direction.

3. The ultrasound diagnostic apparatus according to claim 1, wherein
   a position of a virtual origin where a normal line in the center of the transducer surface along the scan direction and the acoustic line intersect is represented by a function of the beam starting point position, the function being set so that the minimum inter-acoustic line angle is obtained in the center of the ultrasound probe along the scan direction.

4. The ultrasound diagnostic apparatus according to claim 2, wherein the minimum angle is the smallest angle.

5. The ultrasound diagnostic apparatus according to claim 1, wherein the inter-acoustic line angle is smaller toward the center of the ultrasound probe along the scan direction, and the inter-acoustic line angle is larger toward the edges along the scan direction.

6. The ultrasound diagnostic apparatus according to claim 5, wherein the inter-acoustic line angle increases for each pair of acoustic lines from the center toward the edges of the ultrasound probe along the scan direction.

7. The ultrasound diagnostic apparatus according to claim 5, wherein the change of the inter-acoustic line angle is smaller toward the center of the ultrasound probe along the scan direction, and the change of the inter-acoustic line angle is larger toward the edges along the scan direction.

8. The ultrasound diagnostic apparatus according to claim 1, further comprising an image processor that generates the ultrasonic image by spatially synthesizing a plurality of frames obtained by transmitting and receiving ultrasound obtained by deflecting each the acoustic line by a certain angle.

9. An ultrasound diagnostic apparatus that transmits ultrasound toward a subject by driving an ultrasound probe in which a plurality of transducers are arranged in an array, receives a reception signal that is based on waves reflected within the subject from the ultrasound probe, and generates an ultrasound image, the ultrasound diagnostic apparatus comprising:
   a hardware processor that sets a scan condition so that trapezoidal scanning is performed by the ultrasound probe; and
   a transmission section that controls driving of the ultrasound probe based on the scan condition, wherein
   a point where the normal line of a transducer surface in the center of the ultrasound probe along the scan direction and the acoustic line of the ultrasound intersect is defined as a virtual origin, and the hardware processor sets the scan condition so that the virtual origins of the acoustic lines near the edges of the ultrasound probe are closer to the transducer than the virtual origins of the acoustic lines in or around the center, and a position of the virtual origin of a center of the ultrasound probe and a position of the virtual origin of an edge of the ultrasound probe in one frame scan are different.

10. An ultrasound diagnostic method that involves transmitting ultrasound toward a subject by driving an ultrasound probe in which a plurality of transducers are arranged in an array, receiving a reception signal that is based on waves reflected within the subject from the ultrasound probe, and generating an ultrasound image, the ultrasound diagnostic method comprising:

setting a scan condition so that trapezoidal scanning is performed by the ultrasound probe, wherein each acoustic line of a plurality of acoustic lines of the trapezoidal scanning has a different beam starting point where the each acoustic line and a transducer surface of the array of transducers intersect; and controlling driving of the ultrasound probe based on the scan condition, wherein an angle between adjacent acoustic lines is defined as an inter-acoustic line angle, a point where the normal line of a transducer surface in the center of the ultrasound probe along the scan direction and the acoustic line of the ultrasound intersect is defined as a virtual origin, in setting the scan condition, the scan condition is set so that the inter-acoustic line angles in or around the center of the ultrasound probe are smaller than the inter-acoustic line angles near the edges along the scan direction, the acoustic lines are symmetrical about a normal line passing through the center of the transducer surface of the ultrasound probe and the position of the virtual origin of a symmetric pair of the acoustic lines is different from the positions of the virtual origins of the other symmetric pairs of the acoustic lines, and the scan condition is set so that the virtual origins of the acoustic lines near the edges of the ultrasound probe are closer to the transducer than the virtual origins of the acoustic lines in nor around the center.

11. A non-transitory computer-readable recording medium storing a program causing a computer of an ultrasound diagnostic apparatus to execute a predetermined process, the ultrasound diagnostic apparatus transmitting ultrasound toward a subject by driving an ultrasound probe in which a plurality of transducers are arranged in an array, receiving a reception signal that is based on waves reflected within the subject from the ultrasound probe, and generating an ultrasound image, the predetermined process comprising:

setting a scan condition so that trapezoidal scanning is performed by the ultrasound probe, wherein each acoustic line of a plurality of acoustic lines of the trapezoidal scanning has a different beam starting point where the each acoustic line and a transducer surface of the array of transducers intersect; and controlling driving of the ultrasound probe based on the scan condition, wherein an angle between adjacent acoustic lines is defined as an inter-acoustic line angle, a point where the normal line of a transducer surface in the center of the ultrasound probe along the scan direction and the acoustic line of the ultrasound intersect is defined as a virtual origin, in setting the scan condition, the scan condition is set so that the inter-acoustic line angles in or around the center of the ultrasound probe along the scan direction are smaller than the inter-acoustic line angles near the edges along the scan direction, the acoustic lines are symmetrical about a normal line passing through the center of the transducer surface of the ultrasound probe and the position of the virtual origin of a symmetric pair of the acoustic lines is different from the positions of the virtual origins of the other symmetric pairs of the acoustic lines, and the scan condition is set so that the virtual origins of the acoustic lines near the edges of the ultrasound probe are closer to the transducer than the virtual origins of the acoustic lines in nor around the center.

12. The ultrasound diagnostic apparatus according to claim 9, wherein the acoustic lines are symmetrical about a normal line passing through the center of the transducer surface of the ultrasound probe and the position of the virtual origin of a symmetric pair of the acoustic lines is different from the positions of the virtual origins of the other symmetric pairs of the acoustic lines.

13. The ultrasound diagnostic apparatus according to claim 1, wherein an acoustic line angle of each of the acoustic lines meets the following condition:

$\theta = \arctan(PL/PO)$, where the normal line in the center of the transducer surface intersects the transducer surface at an intersection point O, a virtual origin position PO is a distance of the virtual origin from the intersection point O, and acoustic line position PL is a distance between the beam starting point and the center of transducer surface along a scan direction.

14. The ultrasound diagnostic apparatus according to claim 1, wherein a virtual origin position PO of each of the acoustic lines meets the following condition:

$PO = L/\tan\{\text{sgn}(L) \times \beta \times |PL|^\alpha\}$ where the normal line in the center of the transducer surface intersects the transducer surface at an intersection point O, the virtual origin position PO is a distance of the virtual origin from the intersection point O, an acoustic line position PL is a distance between the beam starting point and the center of transducer surface along a scan direction, sgn(L) is a sign of the beam starting point, and α, β are deflection angle variation coefficients relating to the outermost beam starting point position and corresponding acoustic line angle.

* * * * *